United States Patent [19]

Green

[11] Patent Number: 5,171,087
[45] Date of Patent: Dec. 15, 1992

[54] HEATED SUPPORT STAND FOR A STETHOSCOPE

[76] Inventor: Richard D. Green, 12979 Culver Blvd., Los Angeles, Calif. 90066

[21] Appl. No.: 864,311

[22] Filed: Apr. 6, 1992

[51] Int. Cl.⁵ ............................................. F21V 33/00
[52] U.S. Cl. .................................. 362/226; 362/253; 219/242; 219/521
[58] Field of Search ................. 362/226, 253; D26/26; 128/715, 773; 181/131, 141; 219/242, 521, 385, 392, 393

[56] References Cited

U.S. PATENT DOCUMENTS

| D. 323,898 | 2/1992 | Schwartz | D26/26 |
|---|---|---|---|
| 3,443,083 | 5/1969 | Curran | 362/226 |
| 3,766,361 | 10/1973 | Swinyar | 219/521 |
| 4,343,032 | 8/1982 | Schwartz | 362/226 |
| 4,878,162 | 10/1989 | Wu | 362/226 |
| 5,128,518 | 7/1992 | Reifel | 219/521 |

FOREIGN PATENT DOCUMENTS 672412 11/1989 Switzerland .

*Primary Examiner*—Richard R. Cole
*Attorney, Agent, or Firm*—Kelly, Bauersfeld & Lowry

[57] ABSTRACT

A heated support stand is provided for supporting a stethoscope in a convenient and ready-to-use position. The support stand comprises a night light unit having a low wattage bulb disposed behind a protective shade, wherein the shade has a size and shape to receive and support the chestpiece of a stethoscope in close proximity to the bulb. The bulb radiates sufficient heat to warm the chestpiece to a comforable temperature compatible with a patient's body temperature, thus eliminating patient shock and/or discomfort caused by placement of a cold instrument onto the patient's body.

9 Claims, 2 Drawing Sheets

HEATED SUPPORT STAND FOR A STETHOSCOPE

BACKGROUND OF THE INVENTION

This invention relates generally to a simple, convenient, and easy-to-use device for receiving and supporting a stethoscope in a medical examination room or the like, while maintaining the stethoscope chestpiece at a warmed temperature compatible with patient body temperature.

Stethoscopes are commonplace medical equipment used by doctors and auxiliary medical personnel in the course of routine patient examination and/or treatment. In this regard, a stethoscope comprises a chestpiece in the form of a simple mechanical microphone connected via flexible tubing to a headset worn by the attending physician, for purposes of listening to internal sounds produced by the heart, lungs and other internal organs of a patient. The chestpiece is conventionally made from medical grade stainless steel which inherently exhibits relatively high thermal conductivity and thus tends to assume the same temperature as the ambient or room temperature within a medical facility. Unfortunately, modern medical facilities are typically air conditioned, such that the metal chestpiece of the stethoscope quickly assumes the temperature of the surrounding room, with the result that the chestpiece can generate a strong sensation of cold when placed onto the skin of a patient. This cold sensation can frequently be a shock to the patient, causing discomfort and recoil, with resultant increase in patient heart rate and/or blood pressure.

In the past, the problems attributable to a cold stethoscope chestpiece, as discussed above, have been addressed by mounting rubberized rims onto the chestpiece. The rubberized rim material is designed to have a relatively low thermal conductivity and spaces the metal chestpiece from the skin to prevent direct metal-to-skin contact. However, the use of such rubberized rims can decrease the acoustical resolution of the stethoscope. Moreover, rubberized rims are disassembled relatively easily from the chestpiece, and, once removed, are often not re-used.

Accordingly, there is a need for an alternative device which can be used easily and reliably to warm a stethoscope chestpiece to a suitable temperature compatible with patient body temperature. The present invention fulfills these needs and provides other related advantages.

SUMMARY OF THE INVENTION

The present invention resides in a heated support stand for increasing the temperature of a stethoscope chestpiece to a level which is comfortable and compatible with body temperature, such that when the chestpiece is applied onto the body of a patient for auscultation, the patient does not recoil from the chill of the chestpiece against the skin. The support stand comprises, generally, a night light unit having a switch base and a low-wattage light bulb therein, in combination with a protective shade for encasing at least portions of the lamp and for holding the chestpiece in close proximity to the bulb for warming.

In a preferred form of the invention, the night light unit is adapted to plug into an upper socket of a conventional electrical wall outlet. The base includes an on-off switch, and the bulb is threadably engaged into a top portion of the base.

The protective and preferably translucent shade is formed from a heat-resistant material such as molded plastic, and is dimensioned to be unobtrusive and cover the bulb substantially in its entirety to shield it from touch. A slot in the bottom of the shade permits sliding snap-fit mounting onto the top portion of the base. A pair of L-shaped brackets extend from opposite sides of the base and include openings for receiving screws used for secure attachment of the shade to the wall adjacent the electrical outlet. In this manner, the support stand may be affixed to the wall and outlet in a semi-permanent fashion.

The protective shade further includes a groove formed parallel to and near a front end thereof for receiving and supporting the chestpiece in close proximity to the light bulb. A notch may extend forwardly from the groove to accommodate the shape of the chestpiece. In use, the light bulb radiates sufficient heat to warm the chestpiece to a comfortable temperature compatible with body temperature, while additionally providing a convenient night light. The stethoscope headset and related flexible tubing can be supported loosely from the shade for convenient storage in a position ready for immediate use.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
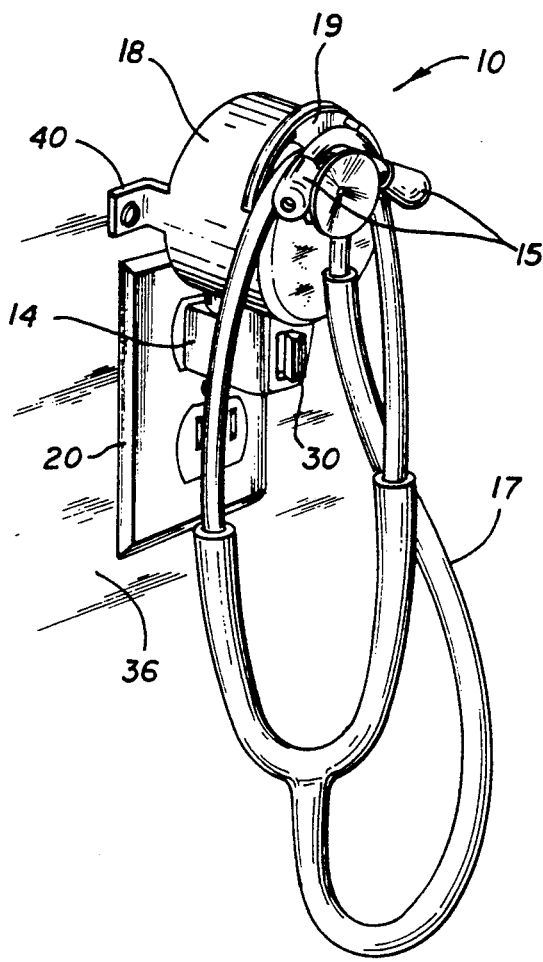
FIG. 1 is a perspective view of a stethoscope mounted on a heated support stand embodying the invention, illustrating the support stand plugged into an electrical wall outlet.
Figure 3:
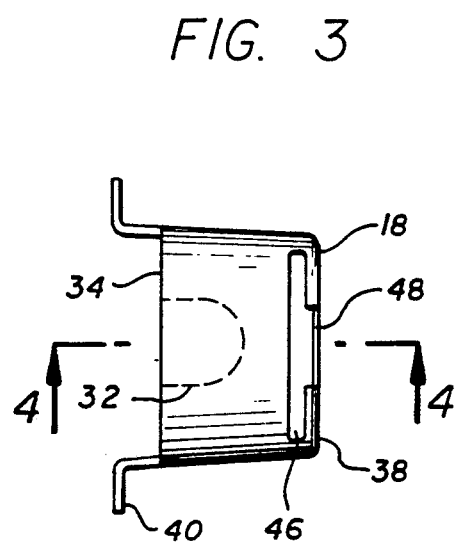
FIG. 3 is a top plan view of a protective shade for the support stand.
Figure 2:
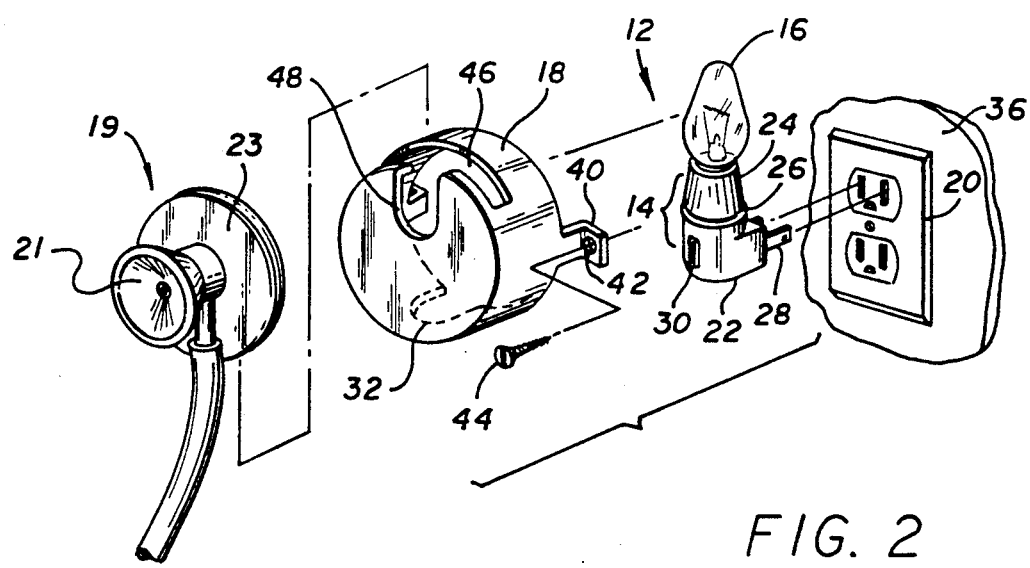
FIG. 2 is an exploded perspective view illustrating construction details of the heated support stand.
Figure 4:
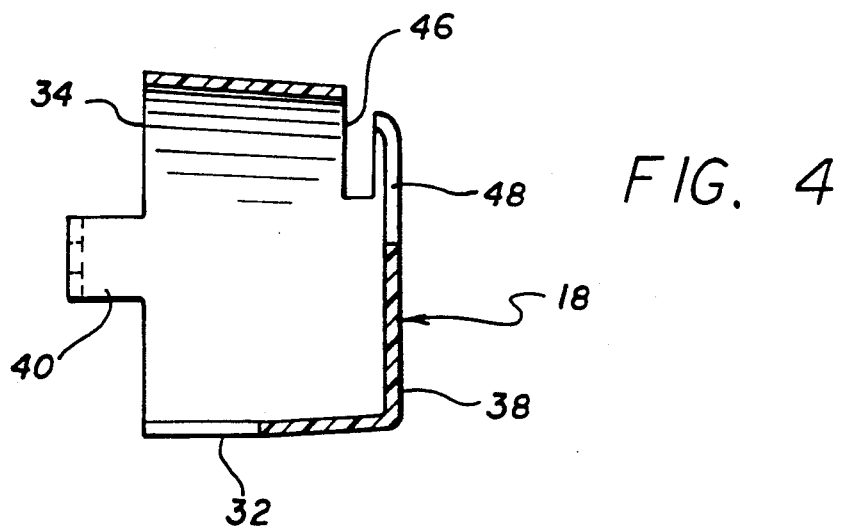
FIG. 4 is a vertical sectional view taken generally along the line 4—4 of FIG. 3.
Figure 5:
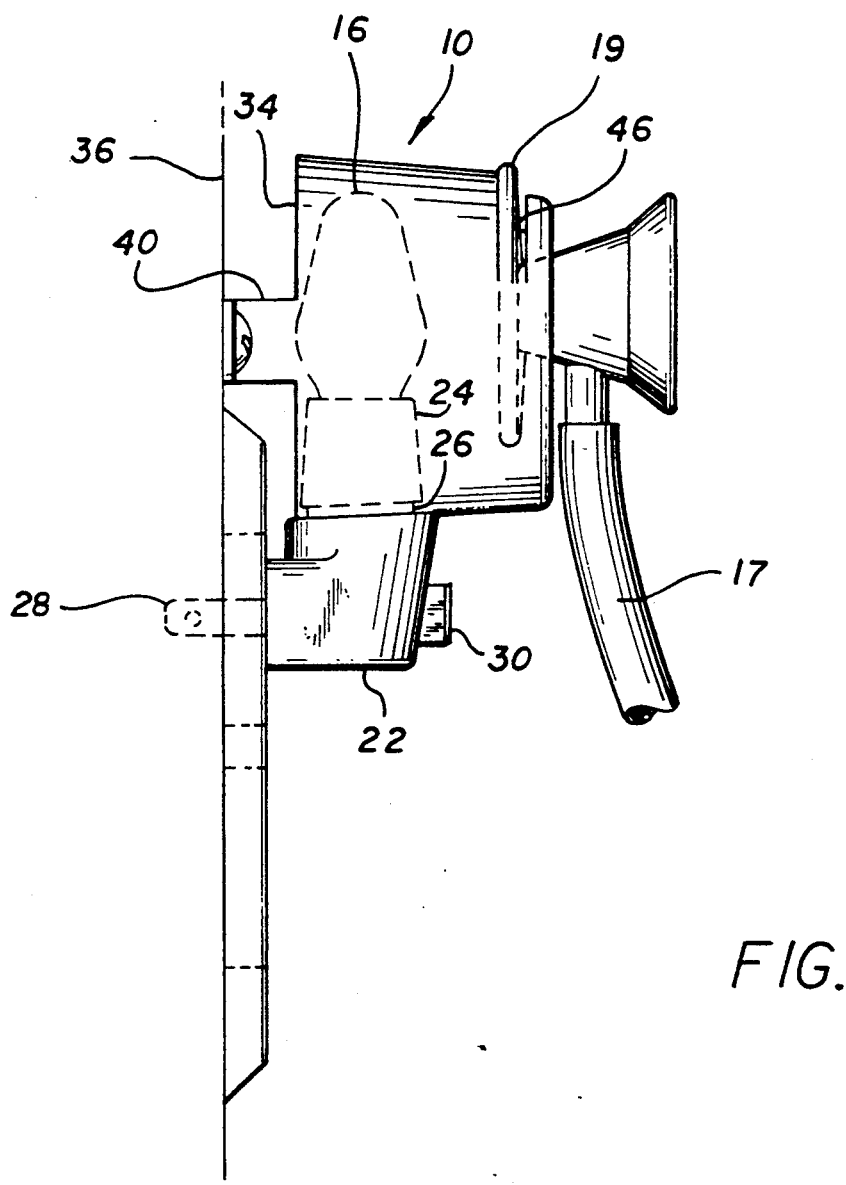
FIG. 5 is a side elevational view of the heated support stand with stethoscope mounted thereon.

As shown in the drawings for purposes of illustration, the present invention is concerned with a heated support stand generally designated in the accompanying drawings by the reference number 10 for warming a stethoscope chestpiece 19. The support stand 10 comprises, generally, a lamp 12 including a night light unit having a base 14 with a light bulb 16, and a protective shade 18 which encases the bulb 16 and holds the stethoscope chestpiece 19 in close proximity to the bulb for warming.

A typical stethoscope used in a modern medical facility by doctors and nurses includes a headset with two earpieces 15, and flexible rubber tubing 17 leading from the headset to the chestpiece 19. The chestpiece 19 comprises a compact mechanical microphone formed typically to include bell side 21 and a diaphragm side 23.

In accordance with the present invention, and as illustrated with respect to a preferred embodiment in FIGS. 1-5, the support stand 10 is configured for plug-in reception to a standard electrical wall outlet 20 for easy accessibility and availability. The support stand 10 generally comprises the night light unit which is adapted to support and warm the stethoscope chestpiece, while additionally performing a conventional night light function.

More particularly, the illustrative night light unit includes the base 14 with a bottom portion 22 and a top portion 24 having a narrow groove 26 formed therebetween. The bottom portion 22 includes a plug 28 extending from the side thereof for reception into the wall outlet 20. An on/off switch 30 is located on an outboard side of the base 14. The top portion 24 of the base 14 is generally cylindrical in shape and includes a socket with suitable internal electrical connections to threadably receive and support the light bulb 16 therein. The light bulb should be low wattage, such as a 4 watt bulb used commonly in traditional night light applications.

The protective shade 18 has a generally cup-shaped configuration and is positioned directly over the top portion 24 of the base 14 to encase the light bulb 16 against direct human contact, thus preventing possible burns. A slot 32 in a lower edge of the shade 18 permits slidable press-fit or snap-fit mounting on the base 14, with the slot 32 defining slot edges which fit into the base groove 26. An open side of the shade 18 faces the adjacent wall 36, with a rear edge 34 set slightly away from the wall by a pair of L-shaped brackets 40 extending from the shade on opposite sides thereof. The brackets 40 each include an opening 42 for receiving a screw 44 therethrough for secure attachment of the shade 18 to the wall 36 above the wall outlet 20. In this manner, the support stand may be affixed to the wall 36 and outlet 20 in a semi-permanent fashion.

The protective shade 18 further includes a narrow groove 46 formed across the top thereof in parallel to and near a front end wall 38. This upper groove 46 is sized and shaped to receive the diaphragm side 23 of the chestpiece 19. A rectangular notch 48 also extends forwardly from the groove 46 to slidably receive the narrow end of the bell side 21 of the chestpiece 19.

The outer dimensions of the shade 18 are made to extend slightly forward from the bulb 16 to keep the chestpiece 19 in close proximity to the bulb 16, but not in direct contact therewith. Such dimensions also make the device relatively inobtrusive and secure when plugged into the outlet. The bulb 16 radiates sufficient heat to warm the chestpiece 19 to a comfortable temperature compatible with body temperature. The shade 18 is constructed of a lightweight molded plastic material that will not deform when subjected to the heat of the bulb, and preferably one of translucent characteristics to permit light radiation for function as a night light. The stethoscope rubber tubing 17 and headset can be wrapped around the shade 18 to provide for continuous storage and warming of the chestpiece (FIG. 1).

From the foregoing, it is to be appreciated that the heated support stand 10 of the present invention provides a convenient device to warm the otherwise cold stethoscope chestpiece making a medical examination more comfortable for the patient.

Although a particular embodiment of the invention has been described in detail for purposes of illustration, various modifications may be made without departing from the spirit and scope of the invention. Accordingly, the invention is not to be limited, except as by the appended claims.

I claim:

1. A heated support stand for a stethoscope chestpiece, comprising:
    a night light unit including a plug-in base for reception into an electrical wall outlet and a light threadably engaged into said base; and
    a protective shade mounted on said base to encase said light bulb, said shade having a groove formed therein for receiving and holding said stethoscope chestpiece in close proximity to the bulb for warming of the chestpiece, said shade further including means for attachment to a wall adjacent the electrical wall outlet.

2. The heated support stand of claim 1 wherein said shade is translucent.

3. A heated support stand for a stethoscope, comprising:
    a night light unit having a base with an upper portion and a lower portion, said upper portion having a socket for receiving a light bulb, said lower portion having a plug for reception into an electrical wall outlet; and
    protective shade means for encasing at least a portion of said bulb, said shade means including means for receiving and supporting a stethoscope chestpiece in close proximity to the bulb, whereby heat radiated from the bulb warms the chestpiece, said shade means further including means for attachment to a wall adjacent the electrical wall outlet.

4. The heated support stand of claim 1, wherein said light bulb is a low wattage bulb.

5. The heated support stand of claim 1, wherein said shade means has a groove formed therein for receiving and supporting the chestpiece.

6. The heated support stand of claim 1 wherein said shade means is formed from a translucent material.

7. The heated support stand of claim 1 wherein said base includes an on/off switch.

8. In combination:
    a stethoscope having a chestpiece; and
    a heated support stand including a night light unit having a plug-in base, a light bulb threadably engaged into said base, and a protective shade mounted on said base generally to encase said light bulb, said protective shade including means for receiving and supporting said chestpiece in close proximity with said bulb whereby heat radiated from said bulb warms said chestpiece.

9. The combination of claim 8 wherein said protective shade has a generally cup-shaped configuration mounted over and substantially encasing said bulb, such that said bulb is positioned within said shade, and further wherein said shade has a groove formed therein generally across a top portion thereof, said chestpiece being seatable within said groove to support and retain said chestpiece generally within said shade and at a position directly adjacent to said bulb.

* * * * *